United States Patent
Blatt

(10) Patent No.: US 11,033,420 B2
(45) Date of Patent: Jun. 15, 2021

(54) OSTOMY POUCH HOLDING SYSTEM

(71) Applicant: Shelby Blatt, Caro, MI (US)

(72) Inventor: Shelby Blatt, Caro, MI (US)

( * ) Notice: Subject to any disclaimer, the term of this patent is extended or adjusted under 35 U.S.C. 154(b) by 453 days.

(21) Appl. No.: 15/990,818

(22) Filed: May 28, 2018

(65) Prior Publication Data

US 2019/0358076 A1    Nov. 28, 2019

(51) Int. Cl.
*A61F 5/449* (2006.01)
*A61F 5/445* (2006.01)
*A61F 5/44* (2006.01)

(52) U.S. Cl.
CPC .............. *A61F 5/449* (2013.01); *A61F 5/445* (2013.01); *A61F 5/44* (2013.01)

(58) Field of Classification Search
CPC combination set(s) only.
See application file for complete search history.

(56) References Cited

U.S. PATENT DOCUMENTS

| | | | | |
|---|---|---|---|---|
| 2,476,513 A | * | 7/1949 | Scott | A61F 5/449 604/345 |
| 2,583,721 A | * | 1/1952 | Beede | A61F 5/449 604/345 |
| 2,595,934 A | * | 5/1952 | Ginsburg | A61F 5/448 604/342 |
| 2,688,327 A | * | 9/1954 | Berg | A61F 5/445 604/333 |
| 3,421,505 A | * | 1/1969 | Freeman | A61F 5/445 604/345 |
| 3,439,677 A | * | 4/1969 | Bonfils Kjeld | A61F 5/441 604/333 |
| 3,893,495 A | * | 7/1975 | Standifer | A61M 5/1417 248/318 |
| 4,122,851 A | * | 10/1978 | Grossner | A61F 5/4408 604/347 |
| 4,331,148 A | * | 5/1982 | Steer | A61F 5/445 604/333 |
| 4,439,191 A | * | 3/1984 | Hogan | A61F 5/445 604/332 |
| 4,495,662 A | * | 1/1985 | Miller | A41D 10/00 2/211 |
| 4,511,358 A | * | 4/1985 | Johnson, Jr. | A61F 5/4404 224/191 |
| 4,533,355 A | * | 8/1985 | Fair | A61F 5/445 2/238 |
| 4,606,736 A | * | 8/1986 | Van De Weghe | A61F 5/44 604/322 |

(Continued)

FOREIGN PATENT DOCUMENTS

WO    WO-2017067557 A2 * 4/2017 ............. A61F 5/448

*Primary Examiner* — Guy K Townsend

(57) ABSTRACT

An ostomy pouch holding system that includes: a first hook; a second hook; a pouch holder, where the pouch holder includes a top opening adapted to receive an ostomy pouch; a bottom opening on the pouch holder; and loop connectors at the top edge, where the loop connectors are adapted to receive the first hook and the second hook. The first hook includes a first button and the second hook includes a second button. The loop connectors preferably include a first loop connector on a first side of the top edge and a second loop connector on a second side of the top edge. The pouch holder is preferably made of spandex. The first hook and second hook are adapted for placement on a waist of a trouser.

1 Claim, 1 Drawing Sheet

(56) References Cited

U.S. PATENT DOCUMENTS

| | | | | |
|---|---|---|---|---|
| D290,403 S * | 6/1987 | Sink | A61F 5/449 | D24/121 |
| 4,705,512 A * | 11/1987 | Faucher | A61F 5/4404 | 604/332 |
| 4,826,495 A * | 5/1989 | Petersen | A61F 5/441 | 604/333 |
| 4,938,747 A * | 7/1990 | Wallace | A61F 5/44 | 604/317 |
| 5,026,362 A * | 6/1991 | Willett | A61F 5/449 | 604/332 |
| 5,032,118 A * | 7/1991 | Mason | A61F 5/4408 | 604/349 |
| 5,135,519 A * | 8/1992 | Helmer | A61F 5/445 | 604/332 |
| 5,135,520 A * | 8/1992 | Beaupied | A41D 13/1254 | 604/345 |
| 5,142,702 A * | 9/1992 | Piloian | A41D 13/1245 | 2/102 |
| 5,234,420 A * | 8/1993 | Horton | A61F 5/4408 | 224/663 |
| 5,248,308 A * | 9/1993 | von Emster | A61F 5/449 | 604/332 |
| 5,454,389 A * | 10/1995 | Hubbard | A61F 5/445 | 134/104.4 |
| D369,662 S * | 5/1996 | Kuentz | A61F 5/449 | D24/118 |
| D377,115 S * | 1/1997 | Feriend | A61F 5/449 | D24/117 |
| 5,626,570 A * | 5/1997 | Gallo | A61F 5/449 | 2/49.2 |
| 5,643,233 A * | 7/1997 | Turner | A61F 5/4408 | 224/663 |
| 5,643,236 A * | 7/1997 | Hadley | A61F 5/4408 | 604/353 |
| 5,651,777 A * | 7/1997 | Walters | A61F 5/449 | 604/345 |
| 5,843,054 A * | 12/1998 | Honig | A61F 5/445 | 604/345 |
| 5,884,771 A * | 3/1999 | McCormick | B65D 85/00 | 206/38 |
| D426,634 S * | 6/2000 | Genshock | A61F 5/449 | D24/118 |
| 6,110,156 A * | 8/2000 | Mendonca | A61F 5/445 | 604/345 |
| 6,231,553 B1 * | 5/2001 | Hulett | A61F 5/441 | 128/DIG. 24 |
| D461,945 S * | 8/2002 | Byrd | A61F 5/449 | D2/860 |
| 6,599,278 B1 * | 7/2003 | Nichols | A61F 5/4408 | 604/179 |
| D508,994 S * | 8/2005 | Hostetler | A61F 5/449 | D24/128 |
| 7,166,091 B1 * | 1/2007 | Zeltner | A61F 5/445 | 604/332 |
| D541,414 S * | 4/2007 | Wallace | A61F 5/449 | D24/118 |
| D544,095 S * | 6/2007 | McLaughlin | A61F 5/449 | D24/118 |
| D618,341 S * | 6/2010 | Massani | A61F 5/449 | D24/118 |
| D636,075 S * | 4/2011 | Yacoub | A61F 5/449 | D24/118 |
| 7,927,320 B2 * | 4/2011 | Goldwasser | A61F 13/82 | 604/344 |
| 8,292,860 B1 * | 10/2012 | Persichetti | A61F 5/44 | 604/355 |
| 8,348,914 B2 * | 1/2013 | Zyburt | A61F 5/449 | 604/317 |
| 8,361,044 B2 * | 1/2013 | Marshall | A61F 5/449 | 604/327 |
| 8,608,718 B1 * | 12/2013 | Patterson-Young | A61F 5/4408 | 604/353 |
| D761,955 S * | 7/2016 | Marshall | A61F 5/449 | D24/118 |
| 2004/0204695 A1 * | 10/2004 | Bisbee | A61F 5/4408 | 604/349 |
| 2004/0215158 A1 * | 10/2004 | Anderson | A61M 39/1011 | 604/327 |
| 2005/0107758 A1 * | 5/2005 | Hogan | A61F 5/449 | 604/327 |
| 2005/0256466 A1 * | 11/2005 | Winkler | A61F 5/449 | 604/337 |
| 2006/0224130 A1 * | 10/2006 | Garrett | A61G 7/0503 | 604/322 |
| 2006/0293631 A1 * | 12/2006 | Bolt | A61F 5/449 | 604/353 |
| 2007/0208314 A1 * | 9/2007 | Barrientos | A61F 5/4404 | 604/353 |
| 2007/0260208 A1 * | 11/2007 | May | A61F 5/4408 | 604/345 |
| 2008/0300556 A1 * | 12/2008 | Fenton | A61F 5/4404 | 604/339 |
| 2010/0205720 A1 * | 8/2010 | Ortega Astor | A41D 13/1281 | 2/247 |
| 2014/0194839 A1 * | 7/2014 | Torres-Leon | A61F 5/4408 | 604/327 |
| 2015/0190198 A1 * | 7/2015 | Debel | A61B 50/37 | 604/344 |
| 2015/0257463 A1 * | 9/2015 | Trimble | A41D 13/1236 | 2/48 |
| 2017/0112658 A1 * | 4/2017 | Hosono | A61F 5/445 | 604/345 |
| 2019/0358076 A1 * | 11/2019 | Blatt | A61F 5/449 | |

* cited by examiner

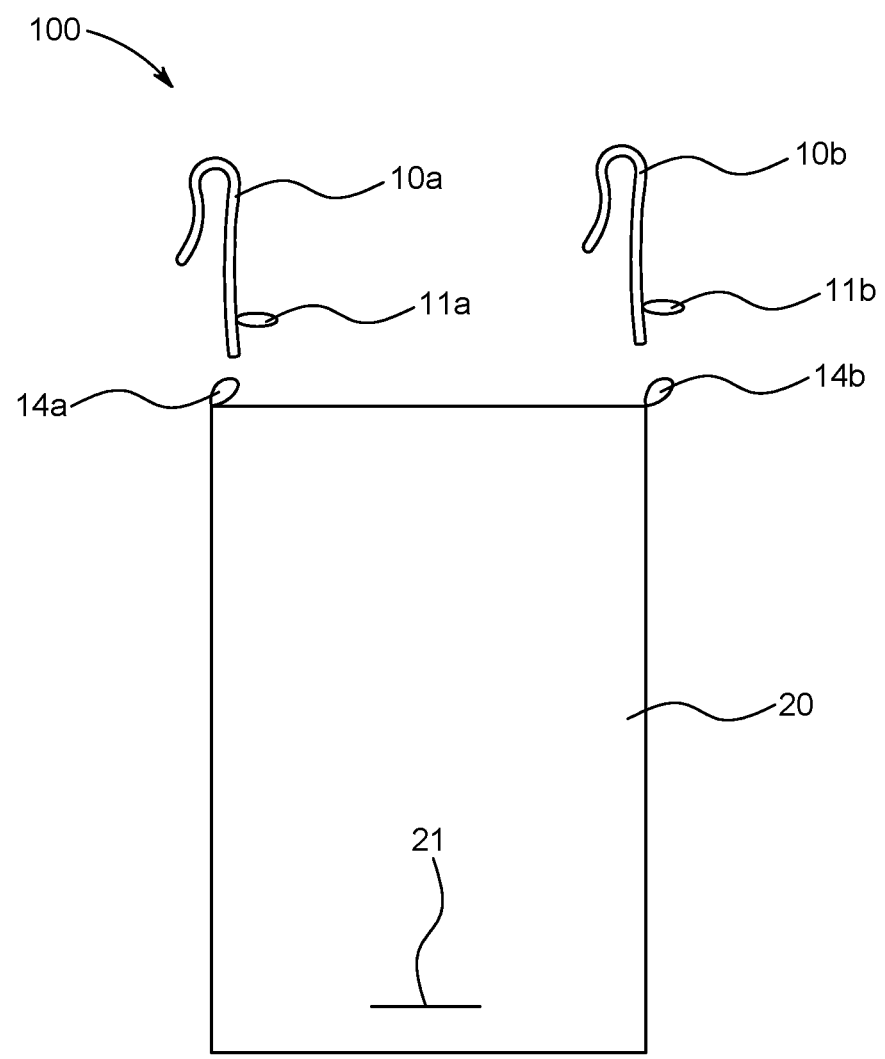

OSTOMY POUCH HOLDING SYSTEM

BACKGROUND OF THE INVENTION

Field of Invention

The present invention relates to an ostomy pouch holding system.

Description of Related Art

An ostomy pouching system provides a means to collect waste from a surgically diverted biological system (colon, ileum, bladder) and the creation of a stoma. Pouching systems are most commonly associated with colostomies, ileostomies, and urostomies.

The pouching systems typically includes a collection pouch plastic bag, known as a one-piece system or, in some instances involves a mounting plate, commonly called a flange, wafer or a baseplate, and a collection pouch that is attached mechanically or with an adhesive in an airtight seal, known as a two-piece system. Ostomy pouching systems collect waste that is output from a stoma. The pouching system allows the stoma to drain into a sealed collection pouch, while protecting the surrounding skin from contamination.

Many patients must utilize an ostomy pouching system and therefore must deal with the various inconveniences associated therewith. The pouch and bag must be placed under clothing and therefore there may be some mobility limitations and problems associated with leakage. The object of the present invention to provide a holding system that includes a pouch that holds the bag in a stationary position and provides the user with more mobility and less limitations while under this type of treatment.

SUMMARY OF THE INVENTION

The present invention relates to an ostomy pouch holding system that includes: a first hook; a second hook; a pouch holder, where the pouch holder includes a top opening adapted to receive an ostomy pouch; a bottom opening on the pouch holder; and loop connectors at the top edge, where the loop connectors are adapted to receive the first hook and the second hook. The first hook includes a first button and the second hook includes a second button. The loop connectors preferably include a first loop connector on a first side of the top edge and a second loop connector on a second side of the top edge. The pouch holder is preferably made of spandex. The first hook and second hook are adapted for placement on a waist of a trouser.

BRIEF DESCRIPTION OF DRAWINGS

FIG. 1 is a view of an ostomy pouch holding system according to the present invention.

DETAILED DESCRIPTION

The present invention relates to a pouch holding system, where the pouch holder is adapted for placement of the inside of a pair of trousers. Hooks are provided at a top edge of the pouch holder that attaches to the waist of the user's trousers. These hooks connect to the pouch holder through the use of loop connectors and buttons provided to connect the hooks to the pouch holder. Preferably the first hook and the second hook are placed at a top edge of the pouch and a button at the distal end of each hook is available for connection. These buttons connect through loop connectors at the top edge of the pouch holder. Once connected the hooks may be placed over the waist edge of the trouser and then placed on the inside of the trousers containing the pouch therein.

The pouch holding system according to the present invention is depicted in FIG. 1. A pouch 20 includes a top opening not shown and a bottom opening 21. The bottom opening 21 is a small slit opening to allow venting of the pouch holder. At the top edge are the first loop connection (14a) and a second loop connector (14b). These loop connectors 14a, 14b provide a means to attach a first hook (10a), the second hook (10b) to the pouch holder (20). The hooks 10a, 10b connect through the use of buttons (11a) on hook (10a) and button (11b) on hook (10b). An ostomy bag may be placed within this pouch for placement on the inside of a trouser. This holding system provides the user with flexibility to use the pouch holder on various types of trousers and helps with the stability to prevent leakage associated with the use of an ostomy pouch.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The exemplary embodiment was chosen and described in order to best explain the principles of the invention and its practical application, to thereby enable others skilled in the art to best utilize the invention and various embodiments with various modifications as are suited to the particular use contemplated.

What is claimed is:

1. An ostomy pouch holding system comprising:
   a. a first hook comprising a first button;
   b. a second hook comprising a second button;
   c. a pouch holder comprising first and second walls forming a cavity and made of Spandex™, wherein the pouch holder includes a top opening spanning a top edge of the pouch holder and adapted to receive a one- or two-piece ostomy pouch sealed to a stoma to collect waste from the stoma, such that the sealed ostomy pouch is contained within the cavity of the pouch holder;
   d. a vent opening slit in a central lower part of the first wall or the second wall of the pouch holder and adjacent to and above a bottom edge of the pouch holder; the slit opening configured to allow venting of gas from the bottom of the pouch holder; and
   e. first and second loop connectors at, respectively, first and second sides of the top edge of the pouch holder, wherein the first and second loop connectors comprise, respectively, first and second loops that are adapted to receive the first and second buttons of the first hook and the second hook;
   wherein the first hook and second hook are configured for placement over a waist of trousers such that the pouch holder with the ostomy pouch therein is placed on the inside of the trousers and held in place by the first and second hooks.

* * * * *